(12) United States Patent
McKim et al.

(10) Patent No.: US 6,660,899 B2
(45) Date of Patent: Dec. 9, 2003

(54) METHODS FOR ENHANCED AROMATIC EXTRACTION EMPLOYING SULFONE-SULFOXIDE COMPOSITIONS

(75) Inventors: Artie S. McKim, Slidell, LA (US); George Kvakovszky, Slidell, LA (US); Michael D. Donahue, The Woodlands, TX (US)

(73) Assignee: Gaylord Chemical Corporation, Slidell, LA (US)

(*) Notice: Subject to any disclaimer, the term of this patent is extended or adjusted under 35 U.S.C. 154(b) by 0 days.

(21) Appl. No.: 09/783,705

(22) Filed: Feb. 14, 2001

(65) Prior Publication Data

US 2003/0045766 A1 Mar. 6, 2003

(51) Int. Cl.$^7$ ............................................. C07C 7/17
(52) U.S. Cl. ........................................ 585/856; 585/857
(58) Field of Search ................................. 585/856, 857

(56) References Cited

U.S. PATENT DOCUMENTS

| | | | |
|---|---|---|---|
| 2,033,942 A | 3/1936 | Kurtz | 208/313 |
| 2,831,039 A | 4/1958 | Nevitt | 206/674 |
| 3,146,190 A | 8/1964 | Papadopoulos | 208/313 |
| 3,466,346 A | 9/1969 | DeGraff | 206/674 |
| 3,714,033 A | 1/1973 | Somekh et al. | 208/321 |
| 3,723,256 A | 3/1973 | Thompson | 203/43 |
| 3,763,037 A | * 10/1973 | Thompson | 208/313 |
| 4,024,028 A | 5/1977 | Haskell | 203/51 |
| 4,053,369 A | 10/1977 | Cines | 203/52 |
| 4,081,355 A | 3/1978 | Preusser et al. | 208/313 |
| 4,292,142 A | 9/1981 | Berg | 203/51 |
| 4,363,704 A | 12/1982 | Berg | 203/58 |
| 4,401,517 A | 8/1983 | Lee | 203/53 |
| 4,498,980 A | 2/1985 | Forte | 208/321 |
| 4,514,262 A | * 4/1985 | Berg | 203/51 |
| 4,676,872 A | 6/1987 | Berg et al. | 202/51 |
| 4,781,820 A | 11/1988 | Forte | 208/313 |
| 4,921,581 A | 5/1990 | Lee et al. | 203/56 |
| 4,948,470 A | 8/1990 | Lee | 203/51 |
| 5,022,981 A | 6/1991 | Forte | 208/334 |
| 5,032,232 A | 7/1991 | Lee et al. | 203/51 |
| 5,085,740 A | 2/1992 | Lee et al. | 203/51 |
| 5,139,651 A | 8/1992 | Forte | 208/534 |
| 5,310,480 A | 5/1994 | Vidueira | 208/213 |
| 5,399,244 A | 3/1995 | Gentry et al. | 203/23 |
| 5,849,982 A | 12/1998 | Lee et al. | 585/833 |

FOREIGN PATENT DOCUMENTS

FR    1407134    6/1995

OTHER PUBLICATIONS

Sucksmith, "Extractive Distillation Saves Energy", Chemical Engineering, pp. 91–95, Jun. 28, 1982.
Maas, "Contiuous Distillation: Separation of Binary Mixtures", Handbook of Separation Techniques for Chemical Engineers, p. 1–135, McGraw Hill, 1979.
Perry's Chemical Engineers Handbook, Extractive Dist 6$^{th}$ Ed., McGraw–Hill Book Company, pp. 13–53 to 13–57, 1984.
Lee, F.M, "Use of Organic Sulfones as the Extractive Distillation Solvent for Aromatics Recovery", Ind. Eng. Chem. Process Des. Dev., 25, 949–957 (1986).
Wu, et al., "Improve Operation and Design of BTX Units", Chemical Engineering, vol. 105, p. 139, Mar. 19998.
Lee, F.M, "Extractive Distillation: Separating Close Boiling Components", Chemical Engineering, vol. 105, p. 112–118 (Nov., 1990).
Barton, F.M., "Solubility Parameters" Chemical Reviews, 75(6), 731–753, (1975).
Barton, F.M.,Handbook of Solubility Parameters and Other Cohesion Parameters, CRC Press, p. 94–110, and 153–161, (1983).
H. Burrel {Polymer Handbook, 2$^{nd}$ Ed., J. Brandrup and E.H. Immergut, Ed, Interscience, New York City, section IV, pp. 337–359(1975).
Hansen, C.J., "The Three Dimensional Solubility Parameter–Key to Paint Component Affinities" (J. Paint Tech. 39, 104–117 (1967).
"Jeffsol" Carbonates, Comparative Solvents Data, published by Huntsman Corporation.
McCormick and Roche, "Continuous Distillation: Separation of Multicomponent Mixtures", *Handbook of Separation Techniques for Chemical Engineers,* Section 1.2, 59–145 (1979).
"DMSO Extraction", Article from Hydrocarbon Processing, Vol 45(9) 223 (1966).
Krause "Dimethyl Sulfoxide Gets Tryout in New Aromatics–Extraction Process" *Chemical Engineering,* 54–56 (Jan. 31, 1966).

\* cited by examiner

*Primary Examiner*—Walter D. Griffin
*Assistant Examiner*—Tam M. Nguyen
(74) *Attorney, Agent, or Firm*—Needle & Rosenberg, PC (57) ABSTRACT

The invention relates to a distillation process composition at least partially separating mixtures of aromatic and non-aromatic hydrocarbon compounds employing an extractive distillation composition comprising:

a. at least one organic sulfoxide of the formula $R_1$—SO—$R_2$, and b. at least one acrylic sulfone of the formula $R_3$—$SO_2$—$R_4$ wherein $R_1$, $R_2$, $R_3$, and $R_4$ have at least one carbon atom and can be the same or different, and
wherein the at least one organic sulfoxide is present in an amount effective to provide improved separation of the aromatic and non-aromatic hydrocarbon compounds, as compared to a process employing the same extractive distillation composition not comprising the organic sulfoxide.

38 Claims, 1 Drawing Sheet

Figure 1

Legend, Figure 1

| Extractive Distillation Composition | Symbol |
|---|---|
| Tetraethylene Glycol | ▲ |
| Sulfolane | ● |
| DMSO | ■ |
| 50:50 DMSO/DMSO2 | ◻ |
| 25:75 DMSO2/sulfolane | ○ |
| 25:75 DMSO2/TEG | △ |

METHODS FOR ENHANCED AROMATIC EXTRACTION EMPLOYING SULFONE-SULFOXIDE COMPOSITIONS

FIELD OF THE INVENTION

This invention relates generally to extractive distillation processes and extractive distillation compositions for enhancing the separation of hydrocarbon compounds via extractive distillation. The extractive distillation compositions comprise both organic sulfoxides and organic sulfones.

BACKGROUND OF THE INVENTION

It is difficult to efficiently and economically separate mixtures of organic compounds having similar chemical characteristics, and nearly the same boiling point and/or volatility. Conventional fractional distillation can be expensive and inefficient in this situation, in that large and expensive columns are required, which have large numbers of plates, and utilize high reflux ratios, with correspondingly high energy consumption rates.

Extractive distillation is a technique for separating certain close boiling mixtures. In extractive distillation, a high boiling extractive distillation solvent is typically introduced into a distillation zone containing feed that is to be separated. The high boiling solvent interacts with the feed mixture (which is typically lower boiling than the extractive distillation solvent) to effectively decrease the volatility of some feed mixture components, typically the more polar feed components, so that the less polar feed components can be separated by distillation overhead. The more polar feed components become relatively concentrated in the extractive distillation solvent/composition, and typically exit the distillation zone as a heavy fraction.

An extractive distillation process has been described in the article entitled "Extractive Distillation Saves Money" by Ian Sucksmith, Chemical Engineering, Jun. 18, 1982, pages 91–95. Other literature sources relating to conventional extractive distillation techniques include the "Handbook of Separation Techniques for Chemical Engineers" by Phillip A Schweitzer, McGraw-Hill Book company, 1984, pages 13–53. A variety of methods for employing extractive distillation to separate various classes of hydrocarbons, such as aromatics, olefins, or cycloalkanes, from other close-boiling hydrocarbons, such as paraffins, are known in the hydrocarbons industry. In particular, many refinery streams comprise "BTX" streams composed of close boiling mixtures of aliphatic hydrocarbons (such as isomers of heptane and octane) and aromatic hydrocarbons (such as benzene, toluene, and xylenes).

A variety of extractive distillation compositions have been reported, and a select few are practiced commercially. The most common of these commercially practiced extractive distillation compositions include polyethylene glycols and mixtures thereof (i.e. "Udex" processes). U.S. Pat. Nos. 3,714,033 and 4,921,581 disclose the use of polyalkylene glycol solvents toward this end. Triethylene glycol and tetraethylene glycol are examples of solvents that are commonly employed in such "Udex" processes.

Other processes for extractive distillation of hydrocarbons have employed organic sulfones as extractive distillation solvents. U.S. Pat. Nos. 2,033,942 and 2,831,039 described the use of dialkyl sulfones, including dimethyl sulfone, in such separations. U.S. Pat. No. 4,401,517 relates to the use of $C_4$–$C_8$ sulfones as selective extractive distillation solvent. U.S. Pat. No. 3,146, 190 described the use of sulfolane (tetramethylene sulfone) as a selective extraction solvent for the purification of pyrolysis fuels and catalytically reformed gasolines. U.S. Pat. Nos. 3,466,346 and 3,723,256 describe refinements of sulfolane-based extractive distillation processes. Sulfolane is also commercially employed as an extractive distillation solvent for the extractive distillation of hydrocarbon compounds.

Dimethyl sulfoxide (DMSO) has also been described as a solvent in extractive distillation applications. Early examples of DMSO based aromatic extraction processes are described in French Patent No. 1,407,134 and by Krause (Chem. Eng. 54–56 (1966)). British Patent No. I373,325 to Rhone-Progil described the use of DMSO to separate mixtures of meta- and para-dichlorobenzene by extractive distillation. U.S. Pat. No. 5,399,244 to Gentry, et al., described the use of aqueous solutions of dimethyl sulfoxide (DMSO) in separating benzene and other aromatic hydrocarbons from mixed aromatic and non-aromatic hydrocarbon streams.

In the commercially practiced embodiments of extractive distillation processes, the solvent (typically triethylene glycol, tetraethylene glycol, sulfolane, and/or DMSO) is believed to be employed in relatively pure form. Nevertheless, there have been reports the use of additives to enhance extractive distillation performance. Water-sulfolane mixtures are disclosed in U.S. Pat. No. 5,849,982. U.S. Pat. No. 5,032,232 describes combinations of N-alkyl-2-thiopyrrolidones and sulfolane for this purpose. U.S. Pat. No. 4,024,028 describes the use of mixtures of dimethyl sulfone, methyl ethyl ketone and sulfolane for the extractive distillation of hydrocarbon mixtures. One study examined the selectivity and solvent power of various DMSO/ethylene glycol mixtures (O. P. Dimitieva et. al., Obshch. Prikl. Chim. 6, 119–122 (1974)). The separation of toluene from close-boiling non-aromatics by extractive distillation with phthalic anhydride in combination with a variety of solvents, including dimethyl sulfoxide, was described in U.S. Pat. No. 4,363,704. Other additives for combination with various extractive distillation solvents have been reported, but many of them are expensive, or have insufficient thermal and/or chemical stability for practical use in extractive distillation compositions.

U.S. Pat. No. 2,831,039 to Nevitt described the use of various short chain (2–4 Carbon) dialkyl sulfones, including dimethyl sulfone, simultaneously with water from about 1 to about 15% by weight, for separating aromatic hydrocarbons from a non-viscous neutral oil containing aromatic and aliphatic hydrocarbons boiling in the gasoline boiling range. Nevitt also disclosed the use of a wide variety of optional diluents, in a concentration range from about 0.1 to about 20% by volume, based on the volume of sulfone solvent employed. Among the many diluents disclosed was dimethylsulfoxide. The above described patents are incorporated hereinbelow by reference in their entirety for their disclosures of extractive distillation compositions and processes.

Polyalkylene glycols or sulfolane are the most widely commercially used extractive distillation solvents used in modern hydrocarbon processing. The glycol systems suffer from relatively low extraction selectivity and aromatic loading capabilities as compared to sulfolane. Polyalkylene glycols also suffer from significant thermal and/or oxidative degradation on an annual basis, and therefore necessitate regular makeup of their volume, which incurs significant expense. Use of sulfolane results in improved extraction selectivity and loading levels, as compared to polyalkylene glycols. Nevertheless, the loading capacity of sulfolane is markedly inferior to that of DMSO, at comparable solvent to hydrocarbon feed ratios. While the use of DMSO results in high capacity, the selectivity of the extractive distillation separation for separation of aromatics from aliphatics is poor as compared to the use of either polyethylene glycols or sulfolane.

It has been estimated that approximately 110 glycol based extractive distillation units and about 75 sulfolane based extractive distillation units are currently being operating commercially worldwide. It is also believed that a handful of DMSO based units operate commercially, primarily in France. Wu et al. estimate (Chemical Engineering, page 139, March 1998) that for a typical industrial BTX extraction unit, a 1% increase in aromatics recovery would result in savings of up to $100,000 per year. Such savings derive from both decreased need for capital investment in equipment, and decreased unit energy requirements (electricity, steam, etc.) needed to perform the extractive distillation.

Thus, both technical and financial considerations provide a continuing need for developing novel and improved extractive distillation compositions. In particular, there is a continuing need for improved extractive distillation processes which could provide a combination of improved selectivity and capacity/loading, as compared to known solvents or compositions and processes.

SUMMARY OF THE INVENTION

The instant invention relates to improved extractive distillation compositions comprising both organic sulfoxides and organic sulfones. The invention also relates to extractive distillation processes that employ the extractive distillation compositions of the invention to at least partially separate mixtures of hydrocarbon compounds. The extractive distillation compositions and/or processes may provide surprising improvements in the separation of certain classes of hydrocarbon compounds, as compared to prior art extractive distillation solvents and/or compositions. The improved separation of the hydrocarbon compounds may be manifested as an unexpectedly large improvement in the selectivity of the separation of the hydrocarbon compounds. The improved separation of the hydrocarbon compounds may also be manifested as an unexpectedly large improvement in the capacity of the extractive distillation composition, i.e. an increase in the loading of certain hydrocarbon compounds in the extractive distillation composition after other hydrocarbon compounds have been removed by extractive distillation. In some embodiments of the invention, use of the extractive distillation compositions of the invention in an extractive distillation process simultaneously and even more unexpectedly provides improvements in both loading and selectivity for the separation of the hydrocarbons, as compared to prior art extractive distillation compositions and processes.

Therefore, in one aspect, the invention relates to an extractive distillation composition for at least partially separating a mixture of hydrocarbon compounds comprising:
a. at least on one organic sulfoxide of the formula $R_1$—SO—$R_2$, and b. at least on one organic sulfone of the formula $R_3$—$SO_2$—$R_4$ wherein $R_1$, $R_2$, $R_3$, and $R_4$ have at least one carbon atom and can be the same or different.

In certain embodiments, the extractive distillation compositions of the invention comprise
a. dimethyl sulfone, and
b. dimethyl sulfoxide.

In another aspect, the invention relates to a process for at least partially separating mixtures of aromatic and non-aromatic hydrocarbon compounds by extractive distillation that employs an extractive distillation composition comprising:
a. at least on one organic sulfoxide of the formula $R_1$—SO—$R_2$, and b. at least on one organic sulfone of the formula $R_3$—$SO_2$—$R_4$ wherein $R_1$, $R_2$, $R_3$, and $R_4$ have at least one carbon atom and can be the same or different, and
wherein the at least one organic sulfoxide is present in an amount effective to provide improved separation of the aromatic and non-aromatic hydrocarbon compounds, as compared to a process employing the same extractive distillation composition not comprising the organic sulfoxide.

In yet another aspect, the invention relates to a process for separating hydrocarbon compounds of similar volatility by extractive distillation, comprising the steps of:
a. contacting a feed mixture with an extractive distillation composition, wherein the feed mixture comprises at least
  i. at least one first hydrocarbon compound, and
  ii. at least one second hydrocarbon compound; and
b. distilling the feed mixture within an extractive distillation zone to at least partially separate the feed mixture into a first stream enriched in the first hydrocarbon compound, and a second stream enriched in the second hydrocarbon compound;
wherein the extractive distillation composition comprises
  i. dimethyl sulfone, and
  ii. greater than about 20 percent by volume of dimethyl sulfoxide.

In yet another aspect, the invention relates to process for at least partially separating hydrocarbon compounds by extractive distillation that employs an extractive distillation composition comprising:
a. greater than about 21% by volume of dimethylsulfoxide, and
b. greater than about 21% by volume of dimethylsulfone.

In one embodiment, the invention provides a process for separating hydrocarbon compounds of similar boiling points by extractive distillation, comprising the steps of:
a. contacting a feed mixture with an extractive distillation composition within an extractive distillation zone, wherein the feed mixture comprises at least
  i. a first hydrocarbon compound, and
  ii. a second hydrocarbon compound; and
b. distilling the feed mixture to at least partially separate the feed mixture into a first stream enriched in the first hydrocarbon compound, and a second stream enriched in the second hydrocarbon compound; and
wherein the extractive distillation composition comprises
  i. at least about 21% by weight of an organic sulfoxide of the formula $R_1$—SO—$R_2$, and ii. at least about 21% by weight of an organic sulfone of the formula $R_3$—$SO_2$—$R_4$ wherein $R_1$, $R_2$, $R_3$, and $R_4$ have at least one carbon atom and can be the same or different.

In yet a different aspect, the invention relates to a process for separating hydrocarbon compounds of similar boiling points by extractive distillation, comprising the steps of:

a. introducing a feed mixture into an extractive distillation zone having an upper portion and a lower portion, wherein the feed mixture comprises at least
  i. a first hydrocarbon compound comprising a $C_7$–$C_{10}$ aliphatic compound, and
  ii. a second hydrocarbon compound comprising benzene, toluene, ortho-xylene, meta-xylene, para-xylene, or a mixture thereof; and
b. introducing an extractive distillation composition into the upper portion of the extractive distillation zone; and
c. distilling the feed mixture to at least partially separate the feed mixture into a first stream rich in the first hydrocarbon compound, and a second stream rich in the second hydrocarbon compound;

wherein the extractive distillation composition comprises:
  i. from about 25 to about 75 parts by weight of dimethylsulfoxide,
  ii. from about 25 to about 75 parts by weight of dimethylsulfone, and
  iii. from about 0.1 to about 15 parts by weight of water.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

The present invention may be understood more readily by reference to the following detailed description of preferred embodiments of the invention and the examples included therein.

Before the present compounds, compositions, articles, devices and/or methods are disclosed and described, it is to be understood that unless otherwise specifically stated by the claims, this invention is not limited to specific synthetic methods, specific types of distillation or fractionation equipment, methods of operating the distillation or fractionation equipment, or to particular ranges of temperature or pressure, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an aromatic compound" includes mixtures of aromatic compounds, references to "a pharmaceutical carrier" includes mixtures of two or more such carriers, and the like.

Ranges may be expressed herein as from "about" one particular value, and/or to "about" another particular value. When such a range is expressed, another embodiment includes from the particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl when there is substitution.

References in the specification and concluding claims to parts by weight of a particular element or component in a composition or article denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5 and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in a polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

The term "alkyl" as used herein refers to a branched or unbranched saturated hydrocarbon of 1 to 24 carbon atoms, such as methyl, ethyl, n-propyl, isopropyl, n-butyl, isobutyl, t-butyl, octyl, decyl, tetradecyl hexadecyl, eicosyl, tetracosyl, and the like. Preferred alkyl groups contain 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms.

The term "aliphatic" as used herein describes branched or unbranched hydrocarbon chains or groups which are saturated, i.e., they have no double bonds between the carbon atoms.

The term "aromatic" as used herein describes substituted or unsubstituted benzene-like compounds of six to twenty five carbon atoms having at least one 6-membered ring residue of carbon atoms, with alternating (conjugated) double bonds which have (4n+2)π electrons, wherein n is a positive integer.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount". However, an appropriate effective amount may be determined by one of ordinary skill in the art using only routine experimentation.

The current inventions, in one aspect, relate to improved extractive distillation compositions for separating a mixture of hydrocarbon compounds.

In one embodiment, the invention relates to extractive distillation compositions for at least partially separating a mixture of hydrocarbon compounds comprising:

a. at least on one organic sulfoxide of the formula $R_1$—SO—$R_2$, and b. at least on one organic sulfone of the formula $R_3$—$SO_2$—$R_4$ wherein $R_1$, $R_2$, $R_3$, and $R_4$ have at least one carbon atom and can be the same or different.

It is to be understood that the at least one organic sulfoxide and/or the at least one organic sulfone may be separately supplied to the extractive distillation processes of the invention and become mixed therein, although they are often supplied as a mixture. It is also to be understood that a mixture two or more organic sulfoxides may be employed. Similarly, it is implied that a mixture of two or more organic sulfones may be utilized.

With respect to the $R_1$, $R_2$, $R_3$, and $R_4$ groups, it is to be understood that these groups are organic radicals that normally have at least one carbon atom, and optional hydrogen atoms. The organic radicals may be present in various forms, which include but are not limited to alkyl hydroxyalkyl, haloalkyl, alkoxy, alkenyl, alkynyl alkylene, aromatic, and/or heteroaromatic groups. The organic radicals may be straight chained or branched, cyclic or acyclic, unsubstituted, or substituted with heteroatoms or heteroatomic groups, such as halide groups, keto groups, sulfide groups, sulfoxide groups, sulfone groups, and the like. The organic radicals may be bonded together to form cyclic groups, including substituted or unsubstituted alkylene groups, to form a cyclic sulfone or sulfoxide. In some embodiments $R_1$, $R_2$, $R_3$, and $R_4$ have from 1 to 12 carbon atoms. Preferably, $R_1$, $R_2$, $R_3$, and $R_4$ have from 1 to 6 carbon atoms. More preferably, $R_1$, $R_2$, $R_3$, and $R_4$ independently have from one to four carbon atoms.

In some embodiments, the organic sulfoxide compound is a dialkyl, diaryl or mixed aryl-alkyl sulfoxide compound. Similarly, in some embodiments, the organic sulfone may be a dialkyl, diaryl or mixed aryl-alkyl sulfone.

In certain embodiments, the extractive distillation includes a dialkyl sulfone having three to nine carbon atoms. Examples of such dialkyl sulfone compounds include methyl ethyl sulfone, methyl propyl sulfone, ethyl propyl sulfone, di-n-propyl sulfone, di-isobutyl sulfone, and the like.

In certain embodiments, the extractive distillation composition include at least one dialkyl sulfoxide having three to nine carbon atoms. Examples of such dialkyl sulfoxide compounds include methyl ethyl sulfoxide, methyl propyl sulfoxide, ethyl propyl sulfoxide, di-n-propyl sulfoxide, di-isobutyl sulfoxide, and the like.

A preferred dialkyl sulfoxide is dimethyl sulfoxide i.e. $CH_3$—SO—$CH_3$ (often abbreviated "DMSO"). DMSO is a high boiling, thermally stable material that is readily commercially available and relatively inexpensive.

A preferred dialkyl sulfone is dimethyl sulfone i.e. $CH_3$—$SO_2$—$CH_3$ (often abbreviated "$DMSO_2$" or "MSM" (an abbreviation for methylsulfonylmethane). $DMSO_2$ is a high boiling, thermally stable material that is readily commercially available and relatively inexpensive. Another preferred organic sulfone compound is sulfolane, i.e. tetramethylene sulfone.

In certain preferred embodiments, the organic sulfoxide is dimethyl sulfoxide and the organic sulfone is dimethyl sulfone.

The invention also generally relates to processes for extractive distillation which employ the extractive distillation compositions of the invention. The extractive distillation processes of this invention are not necessarily limited (unless otherwise explicitly indicated by the claims) to any particular set of steps, apparatus, and/or operating procedures for extractive distillation, as many variations of such steps, apparatus, and/or procedures are known to those of skill in the art, and are disclosed, inter alia, in the above-referenced patents. Both batch and continuous extractive distillation processes are within the scope of the instant inventions. Similarly, the extractive distillation processes employing the instant extractive distillation compositions are not necessarily limited to separating any particular combinations or mixtures of hydrocarbon substrates, as the prior art discloses many such combinations of hydrocarbon substrates that may be advantageously separated by the instant extractive distillation processes and compositions.

In one aspect the invention provides a process for at least partially separating mixtures of aromatic and non-aromatic hydrocarbon compounds by extractive distillation that employs an extractive distillation composition comprising:

a. at least on one organic sulfoxide of the formula $R_1$—SO—$R_2$, and b. at least on one organic sulfone of the formula $R_3$—$SO_2$—$R_4$ wherein $R_1$, $R_2$, $R_3$, and $R_4$ have at least one carbon atom and can be the same or different.

In another aspect, the invention relates to a process for separating hydrocarbon compounds of similar volatility by extractive distillation, comprising the steps of:
a. contacting a feed mixture with an extractive distillation composition, wherein the feed mixture comprises at least
    i. at least one first hydrocarbon compound, and
    ii. at least one second hydrocarbon compound; and
b. distilling the feed mixture within an extractive distillation zone to at least partially separate the feed mixture into a first stream enriched in the first hydrocarbon compound, and a second stream enriched in the second hydrocarbon compound;
wherein the extractive distillation composition comprises
    i. dimethyl sulfone, and
    ii. dimethyl sulfoxide.

In one preferred embodiment, the invention relates to a process for at least partially separating hydrocarbon compounds by extractive distillation that employs an extractive distillation composition comprising:

a. greater than about 21% by volume of dimethylsulfoxide, and b. greater than about 21% by volume of dimethylsulfone.

It has been found that both the identity of, and absolute and/or relative proportions of the at least one organic sulfoxides and at least one organic sulfones may have an unexpectedly beneficial effect on the efficiency of the separations achieved in the extractive distillation processes. Therefore in some embodiments, the identities and/or amounts of the at least one organic sulfoxide (including dimethylsulfoxide) and the at least one organic sulfone (including dimethylsulfone) are selected to provide effective separation of a particular mixture of hydrocarbon compounds. In some embodiments, an amount of the organic sulfoxide is selected that is effective to provide improved separation the hydrocarbon compounds, as compared to a process employing the same extractive distillation composition not comprising the organic sulfoxide.

Similarly, an amount of the organic sulfone may be selected that is effective to provide improved separation of the hydrocarbon compounds, as compared to a process employing the same extractive distillation composition not comprising the organic sulfone. In some preferred embodiments, the amounts of both the organic sulfone and the organic sulfoxide are simultaneously selected to provide improvement in the separations.

The improved separation of the hydrocarbon compounds may, in some embodiments, be manifested as an increase in the selectivity of the separation of the hydrocarbon compounds. The selectivity of the separation of two or more hydrocarbon compounds (or classes of hydrocarbon compounds) can be calculated as the numerical ratio of the concentrations of the compounds present in the process stream containing the bulk of the extractive distillation composition, that is a product of the extractive distillation process. It is of particular interest that high selectivity be achieved for the separation of aromatic compounds from non-aromatic compounds, including aliphatic compounds. Thus, one method for determining the selectivity of the separation for aromatic versus aliphatic compounds is to collect a sample of the process phase or stream containing the bulk of the extractive distillation composition produced by the extractive distillation, and experimentally measuring the concentrations of the aromatic and aliphatic compounds contained therein. The selectivity of the extractive distillation solvent/composition may then be calculated as:

$$\text{Selectivity} = \{[\text{aromatics}]_{solvent}/[\text{aliphatics}]_{solvent}\}$$

wherein "solvent" refers to the phase or process stream containing the bulk of the extractive distillation solvent and/or composition.

In view of the teachings of Wu et al. (discussed above) significant economic benefits may be obtained by increasing the selectivity of the separation of hydrocarbon compounds by as little as about 1%. Preferably, the increase in the selectivity of the separation of the hydrocarbon compounds may be greater than about 3%, greater than about 5%, or greater than about 10%.

The improved separation of the hydrocarbon compounds in the processes of the invention may, in some embodiments, be manifested as an increase in the "loading" of certain desired hydrocarbon compounds in the phase or stream containing the extractive distillation phase, after the extractive distillation. For embodiments relating to the separation of aromatic compounds from non-aromatic compounds, 'Loading' relates to the absolute quantity (such as the weight) of aromatic compound(s) extracted into a specified quantity of the extractive solvent phase during or after an extractive distillation. In the examples disclosed herein below, the "loading" was measured by quantitating the weight of an extracted aromatic (toluene) contained in the extractive solvent phase that resulted after the extractive distillation process.

Therefore, in some embodiments of the instant invention, the improved separation of the hydrocarbon compounds comprises an increase in the loading of the desired hydrocarbon compounds in the extractive distillation composition after extractive distillation. Significant benefits may be obtained by increasing the loading of the hydrocarbon compounds by as little as about 1%. Preferably, the increase in the selectivity of the separation of the hydrocarbon compounds may be greater than about 3%, greater than about 5%, or greater than about 10%.

In certain preferred embodiments, the improved separation of the hydrocarbon compounds comprises an increase in both the selectivity of the separation of the hydrocarbon compounds, along with a simultaneous increase the loading of the desired hydrocarbon compounds in the extractive distillation composition after extractive distillation.

The specific amounts of the organic sulfoxide and/or organic sulfone that provide useful and/or optimum improvements in separation will of course vary with nature of the hydrocarbons to be separated, the temperature, the details of the extractive distillation process employed, and other variables. Nevertheless, such amounts may be determined with only routine experimentation for any particular selection of hydrocarbon compounds and/or any particular embodiment of an extractive distillation process steps.

In some embodiments, the at least one organic sulfoxide (including dimethylsulfoxide) is present at a concentration of greater than about 20 percent by weight, or by volume, or preferably at a concentration of greater than about 21 percent by weight, or by volume. Preferably, the at least one organic sulfoxide may be present at a concentration of from about 21 to about 95 weight percent. In other embodiments, the at least one organic sulfoxide is present at a concentration of from about 22 to 78, 25 to about 75 weight percent, or from about 30 to about 70 weight percent.

Similarly, in some embodiments, the at least one organic sulfone (including dimethylsulone) is present at a concentration of greater than about 20 percent by weight or volume, or preferably at a concentration of greater than about 21 percent by weight, or by volume. Preferably, the at least one organic sulfone is present at a concentration of from about 22 to about 78 weight percent. In other embodiments, the at least one organic sulfoxide is present at a concentration of from about 25 to about 75 weight percent, or from about 30 to about 70 weight percent.

Figure 1:
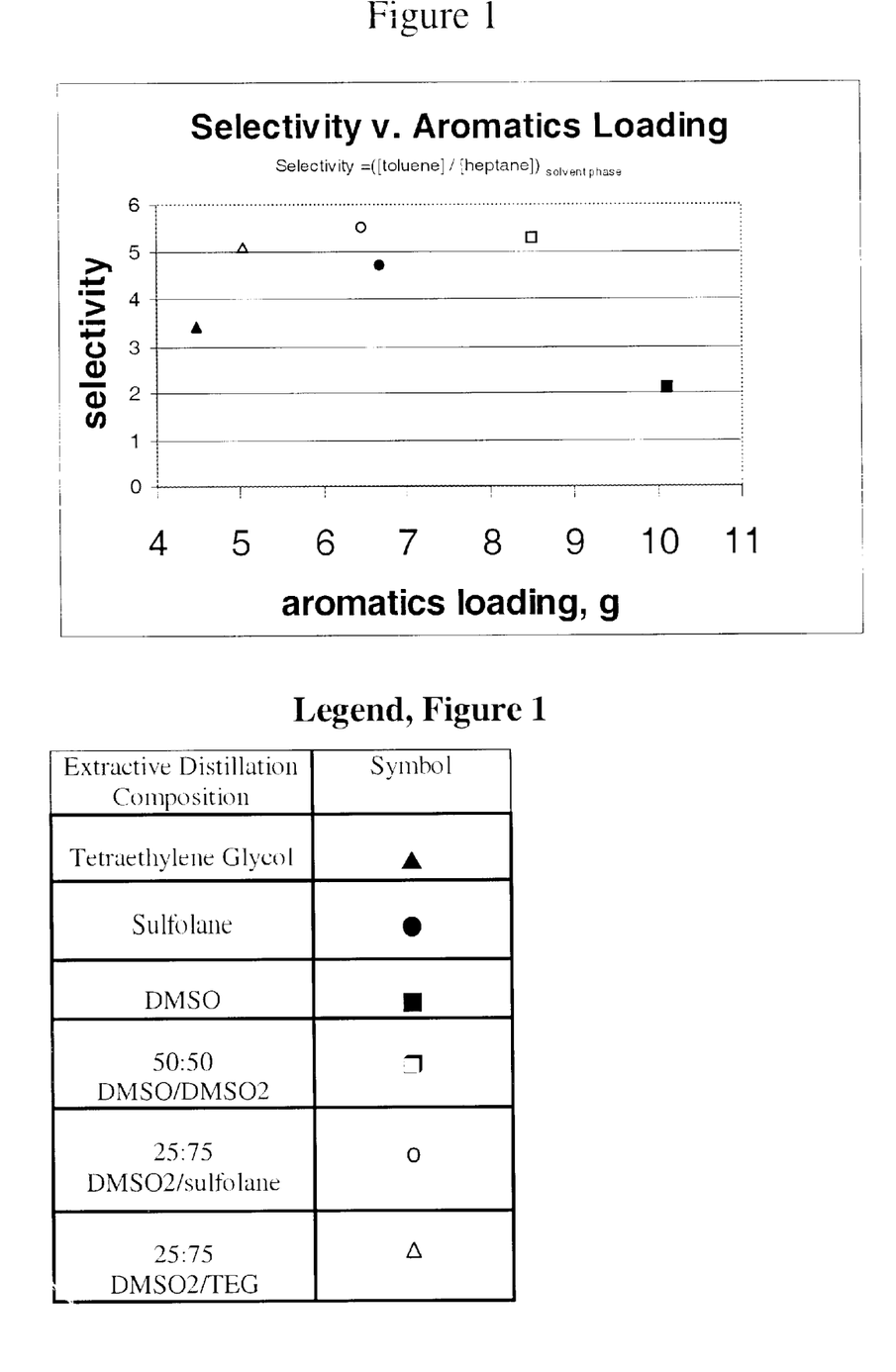
FIG. 1. shows the advantage (as measured by selectivity and aromatics loading) of certain DMSO-$DMSO_2$ mixtures as an extractive distillation solvent, relative to tetraethylene glycol, sulfolane and DMSO, respectively.

Embodiments comprising both dimethylsulfone and dimethylsulfoxide have been found to give unexpectedly superior results in the separation of aromatic compounds from aliphatic compounds, relative to the results obtained from extractive solvents previously available to refinery science, such as polyalkylene glycols, sulfolane, or dimethylsulfoxide. We have found that while the use of dimethyl sulfoxide alone results in high aromatics loading characteristics, the selectivity of dimethylsulfoxide alone for the separation of aromatic and nonaromatic hydrocarbons is poor, as shown in FIG. 1. Surprisingly, we have found that the addition of appropriate quantities of dimethyl sulfone to known extractive distillation solvents can dramatically increase the selectivity of the separation. See FIG. 1, wherein the addition of dimethylsulfone to either ether tetraethylene glycol or sulfolane increased the selectivity of both those extractive distillation solvents. We have also discovered that the addition of dimethylsulfone to dimethylsulfoxide dramatically increases the selectivity, while maintaining much of the loading capacity of the dimethylsulfoxide. As shown in FIG. 1, a mixture of 50:50 dimethylsulfoxide/dimethylsulfone has both a substantially improved selectivity and loading capacity, as compared to either sulfolane or polyethylene glycols. Such simultaneous increases in selectivity and loading can significantly improve the energy consumption and capacity of a commercial extractive distillation unit.

In some embodiments, the extractive distillation composition further comprises water. Minor amounts of water may improve the selectivity of extractive distillation compositions for separation of the hydrocarbon compounds, lower the boiling point of the extractive distillation composition, and/or improve miscibility of the components of the extractive distillation composition. Preferred embodiments of the extractive distillation composition of the invention may comprise from about 0.1 to about 15% by weight of die water. More preferably, the extractive distillation composition further comprises from about 0.5 to about 3% by weight of the water.

The extractive distillation compositions used in the instant methods may also advantageously comprise conventional additives, including surfactants, corrosion inhibitors, or antioxidants.

In certain embodiments of the processes of the invention, the feed mixture is introduced into an extractive distillation zone, which often has an upper portion and a lower portion. The extractive distillation zones suitable for the invention can comprise a wide variety of equipment and devices suitable for distillation processes, such as tanks, vessels, pipes, tubing, heat exchangers, reboilers, wiped film or falling film evaporators, distillation columns, and the like. The extractive distillation zones are often provided with means for ensuring intimate physical contact between the feed mixtures and the extractive distillation composition during the extractive distillation process, such as trays, packing materials, condensers, and the lie. The extractive distillation zones often comprise distillation columns, the design and operation of which are well known to those of skill in the art. The distillation columns may be packed with various materials which provide high surface areas, and/or ensure a tortuous path for inducing the contact of gases and liquids. The distillation columns may also have trays, which collect liquid and have means for inducing the interaction of the liquid with vapors within the column.

Many embodiments of the extractive distillation processes of the invention comprise introducing the extractive distillation composition into the upper portion of an extractive distillation zone, so that it may flow downward as the distillation occurs, and intimately contact with the feed mixture. The feed mixture is preferably introduced into a lower portion of the extractive distillation zone, so that the more volatile components vaporize and flow upward in the distillation zone. Preferably, the extractive distillation composition is not introduced at the uppermost portion of the extractive distillation zone, so as to ensure that it does not contaminate the overhead stream, which is typically enriched in the more volatile and/or less polar components of the feed mixture, such as the first hydrocarbon compound. In a preferred embodiment, the extractive distillation process further comprises withdrawing the overhead stream from the upper portion of the extractive distillation zone.

The pressure in the extractive distillation zone may be subatmospheric, approximately atmospheric, or superatmospheric. Preferably, the pressure in the extractive distillation zone is from about 1 atmosphere to about 5 atmospheres.

The feed mixtures utilized in the extractive distillation processes can include complex mixtures of wide varieties of chemical compounds and/or hydrocarbons. Typically, the compounds comprise mixtures of hydrocarbon compounds and/or petroleum distillates, which may be unsubstituted, or substituted with a wide variety of alkyl groups, alkylene groups, aromatic groups, heteroatoms (including oxygen, nitrogen, silicon, sulfur, phosphorus or halogens), or heteroatomic groups or residues which contain heteroatoms. The hydrocarbon compounds may be branched or unbranched, saturated or unsaturated, cyclic or heterocyclic, aromatic, or substituted aromatic compounds.

In some embodiments, the feed mixture comprises a first hydrocarbon compound of relatively low polarizability, and a second hydrocarbon compound having relatively higher polarizability. The feed mixture may also comprise hydrocarbon compounds (and/or their isomers) with differing polarities. One example of isomeric hydrocarbons having different polarities are para-xylene and ortho-xylene. In some embodiments, the first hydrocarbon compound comprises at least one saturated hydrocarbon residue (exemplified by alkyl residues such as methyl, ethyl, or higher alkyl groups), and a second hydrocarbon compound comprising at least one carbon—carbon double bond (such as mono-olefins, polyolefins, and/or aromatics).

In many embodiments, the extractive distillation process at least partially separates the feed mixture into a first stream enriched in the first hydrocarbon compound, and a second stream enriched in the second hydrocarbon compound. Often, the first hydrocarbon compound is relatively non-polar as compared to the second hydrocarbon compound. While not wishing to be bound by theory, it is believed that the second hydrocarbon compound, which is more polar, typically interacts more strongly with the extractive distillation composition, and therefore selectively combines with the extractive distillation composition, to produce the second stream In many embodiments, the second stream exits the extractive distillation zone from a lower portion of the distillation zone, to form a "bottoms" stream The bottoms steam preferably comprises a mixture of the extractive distillation composition and the second hydrocarbon compound. Preferably, the bottoms stream is selectively enriched in the second hydrocarbon compound and relatively depleted in the first hydrocarbon compound, as compared with the feed mixture.

In contrast to the second hydrocarbon compound, the typically less polar first hydrocarbon compound often interacts less strongly with the extractive distillation composition. As a result, the volatility of the first hydrocarbon compound is not greatly depressed, so that it preferentially vaporizes, and its concentration is enhanced in the first stream, that typically exits the extractive distillation zone from an upper portion of the extractive distillation zone, to form an "overhead" stream.

In one embodiment, the extractive distillation process further comprises withdrawing the second stream from the lower portion of the extractive distillation zone. In another preferred embodiment, the extractive distillation process further comprises treating the bottoms stream to separate the second hydrocarbon compound from the extractive distillation composition. The treatment that separates the second hydrocarbon compound from the extractive distillation composition often comprises an additional distillation or extraction process.

In a preferred embodiment, the feed mixture comprises a mixture of aliphatic and olefinic compounds, wherein the first hydrocarbon compound is an aliphatic compound or mixture of aliphatic compounds, and the second hydrocarbon compound is an olefinic compound or a mixture of olefinic compounds. In another preferred embodiment, the first hydrocarbon compound comprises at least one saturated hydrocarbon residue, and the second hydrocarbon compound comprises at least one carbon-carbon double bond.

In certain embodiments, the first hydrocarbon compound is a $C_7$–$C_{10}$ aliphatic compound. In other embodiments, the saturated hydrocarbon residue of the first hydrocarbon compound comprises at least two carbon atoms.

In many embodiments, the second hydrocarbon compound comprises an aromatic residue. In more preferred embodiments, the second hydrocarbon compound is a $C_6$–$C_{10}$ substituted benzene compound. In certain highly preferred embodiments, the second hydrocarbon compound is benzene, toluene, ortho-xylene, meta-xylene, para-xylene, ethylbenzene, or a mixture thereof.

In many preferred embodiments of the invention, the feed mixture comprises a mixture of aliphatic, olefinic, and/or aromatic compounds. Such mixtures are common in the hydrocarbon and oil refining industries, and are often produced in pyrolysis gasoline units, or catalytic reforming units. In one highly preferred embodiment, the feed mixture comprises a BTX stream BTX streams are very common in petroleum and hydrocarbon refining and recovery processes, and comprise mixtures of benzene, toluene, para-xylene, meta-xylene, ortho-xylene, or ethylbenzene, as well as other saturated hydrocarbons or olefins having normal boiling points similar to those of benzene, toluene, para-xylene, meta-xylene and ortho-xylene. The saturated hydrocarbons of BTX streams typically comprise mixtures of isomeric $C_6$–$C_{10}$ alkanes and/or olefins. In refinery operations, the aromatic compounds generally are of higher value, and one objective of extractive distillation of BTX streams is to selectively purify and/or recover the aromatics from mixtures. A selective extractive distillation solvent often enhances the concentration of aliphatic/non-aromatic materials in the extractive distillate (raffinate, in refinery parlance) relative to that of the aromatic components.

In another preferred embodiment, the feed mixture comprises ethylbenzene, styrene, or a mixture thereof.

Although extractive distillation is often applied to separate a wide variety of mixtures of hydrocarbon compounds, including very complex multi-component mixtures, or azeotropic mixtures (which form in either the presence or absence of water), extractive distillation is often employed when certain components of the hydrocarbon mixture have similar normal boiling points or volatilities. In preferred embodiments of the processes of the invention, the first and second hydrocarbon compounds have normal boiling points that differ by less than about 5° C. More preferably, the first and second hydrocarbon compounds have normal boiling points that differ by less than about 2° C.

One embodiment of the invention provides a process for separating hydrocarbon compounds of similar boiling points by extractive distillation, comprising the steps of:
 a. introducing a feed mixture into an extractive distillation zone having an upper portion and a lower portion, wherein the feed mixture comprises at least
  i. a first hydrocarbon compound comprising a $C_7$–$C_{10}$ aliphatic compound, and
  ii. a second hydrocarbon compound comprising benzene, toluene, ortho-xylene, meta-xylene, para-xylene, ethylbenzene or a mixture thereof; and
 b. introducing an extractive distillation composition into the upper portion of the extractive distillation zone; and
 c. distilling the feed mixture to at least partially separate the feed mixture into a first stream rich in the first hydrocarbon compound, and a second stream rich in the second hydrocarbon compound;
wherein the extractive distillation composition comprises:
  i. dimethylsulfoxide, and
  ii. greater than about 21% by weight of dimethylsulfone, and
  iii. from about 0 to about 15 parts by weight of water.

In yet a different aspect, the invention relates to a process for separating a mixture of hydrocarbon compounds by extractive distillation that employs an extractive distillation composition, wherein the improvement comprises the use of a mixture comprising at least one organic sulfoxide compound and at least one organic sulfone compound.

In alternative aspects, the invention provides the products produced by the extractive distillation processes of the invention. The products of the processes of the invention preferably comprise the first stream, the second stream, the high purity hydrocarbon compounds produced by further treatment of the first or second streams, and the extractive distillation composition recovered from the extractive distillation zone. In many embodiments, any extractive distillation composition so recovered is recycled to an extractive distillation zone.

The extractive distillation compositions and extractive distillation processes of the invention often have the advantage of ready implementation in existing aromatic extraction units, which are common in the refineries and manufacturing facilities of the chemical and hydrocarbon industries. The improvements and advantages (such as increased product capacity and lower utility and energy costs) are often obtained at relatively low capital cost. The raw material requirements of the process of this invention also compare favorably with that of conventional processes, and can offer improved extractive solvent loading and/or enhanced extraction selectivity than the extractive distillation solvents currently in use in the hydrocarbon industry.

Experimental

The following examples are put forth so as to provide those of ordinary skill in the art with a complete disclosure and description of how the compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Protocol for Extractive Distillation Selectivity Experiments

A hydrocarbon mixture containing 0.5 parts by weight of toluene and 0.5 parts of n-heptane, was combined with four parts by weight of an extractive distillation composition (of a specified composition comprising a sulfone and a sulfoxide, and/or water), and placed in a distillation apparatus designed to vaporize, then condense and collect an overhead extractive distillate phase. The quantity of the mixture was held essentially constant between experiments, to eliminate differences attributable to heating and distillation effects in the apparatus. The mixture was then heated to its boiling point, and a measured volume of the extractive distillate phase (hydrocarbon raffinate) was collected, and analyzed using gas chromatography for heptane and toluene. Selectivity is quantified in the cited examples as the ratio of the weight percent concentrations of aromatic to aliphatic components in the extractive solvent phase.

Thus, selectivity of the solvent system was calculated as:

Selectivity={[toluene]$_{solvent}$/[heptane]$_{solvent}$}

Solvent loading was measured by quantitating the weight of extracted aromatic (toluene) contained in the extractive solvent phase.

Loading=Weight toluene$_{solvent}$

Experiments without a sulfone (i.e. control experiments) were also performed, and the results compared to experiments which used a mixture of sulfone and sulfoxide.

EXAMPLE 1

50:50 Dimethyl Sulfoxide—Dimethyl Sulfone Experiment

An Othmer type equilibrium cell was employed consisting of a stillpot, overhead condenser, sampling ports and condensate collection spoon. Combined in the equilibrium cell at room temperature were 60.0 g dimethyl sulfoxide and 60.0 g dimethyl sulfone. The solvent blend was warmed at ca. 40° C. with magnetic stirring to completely dissolve the sulfone. A mixture, 30.0 g of 1 part toluene to 1 part n-heptane was added, and the heating was increased to bring the mixture to reflux. Reflux continued for 15 minutes in the closed system; at this point the vapor temperature was 100–101° C.

The condensate collection spoon was inverted to collect a sample of condensed vapor below the water condenser, and a syringe needle was used to withdraw a sample for analysis through the sample port. Similarly, samples of both the solvent and feed phases were withdrawn by syringe through the lower sample port for GC analysis. The solvent and feed phase samples were diluted with acetone prior to GC analysis; the vapor condensate sample was analyzed neat. Values for solvent, feed, and vapor phase compositions were reported as an average of two experiments.

Analysis was performed on a Hewlett-Packard 6890 gas chromatograph fitted with a 15M Quadrex column (100% methylsilicone, 3.0 mm film thickness, 0.32 mm i.d.). Inlet temperature was set to 250° C., Detector (FID) temperature set at 275° C. Initial run temperature was 70° C. (hold 15 min), followed by a 10 C/min ramp rate to 100° C. (hold 10 min). The last portion of the run included a 10 C/min. ramp rate to 150° C. (hold 27 min.).

Aliquots of the mixture were withdrawn at reflux and analyzed by Gas Chromatography for wt % toluene and wt % n-heptane.

The following results were obtained:

TABLE 1

Liquid-liquid Equilibrium (LLE) data for DMSO/DMSO$_2$ mixtures.

|  | wt % toluene | wt % heptane |
|---|---|---|
| Solvent phase | 13.2 | 2.6 |
| Feed phase | 35.6 | 64.4 |

Thus, one may calculate selectivity, that is, the ratio of aromatics to aliphatics in the solvent phase at 5.08.

[toluene]$_{solvent}$/[heptane]$_{solvent}$=13.2/2.6=5.08

EXAMPLE 2

Dimethyl Sulfoxide Control Experiment

Charged in the equilibrium cell at room temperature was 120.0 g dimethyl sulfoxide. A mixture, 30.0 g of 1 part toluene to 1 part n-heptane was added, and the heating was increased to bring the mixture to reflux. Reflux continued for 15 minutes in the closed system; At this point the vapor temperature was 100–101° C. Samples of both the solvent and feed phases were withdrawn by syringe through the lower sample port for GC analysis. The solvent and feed phase samples were diluted with acetone prior to GC analysis; the vapor condensate sample was analyzed neat. Values for solvent, feed, and vapor phase compositions were reported as an average of two experiments.

The following results were obtained:

TABLE 2

Liquid-liquid Equilibrium (LLE) data for DMSO experiment.

|  | wt % toluene | wt % heptane |
|---|---|---|
| Solvent phase | 12.62 | 5.64 |
| Feed phase | 73.0 | 27.8 |

Thus, one may calculate selectivity, that is, the ratio of aromatics to aliphatics in the solvent phase at 1.98.

[toluene]$_{solvent}$/[heptane]$_{solvent}$=12.62/5.64=2.24

EXAMPLE 3

Sulfolane Control Experiment

Charged in the equilibrium cell at room temperature was 120.0 g sulfolane. A mixture, 30.0 g of 1 part toluene to 1 part n-heptane was added, and the heating was increased to bring the mixture to reflux. Reflux continued for 15 minutes in the closed system; at this point the vapor temperature was 100–101° C. Samples of both the solvent and feed phases were withdrawn by syringe through the lower sample port for GC analysis. The solvent and feed phase samples were diluted with acetone prior to GC analysis; the vapor condensate sample was analyzed neat. Values for solvent, feed, and vapor phase compositions were reported as an average of two experiments.

The following results were obtained:

TABLE 3

Liquid-liquid Equilibrium (LLE) data for sulfolane experiment.

|  | wt % toluene | wt % heptane |
|---|---|---|
| Solvent phase | 10.64 | 2.25 |
| Feed phase | 27.31 | 69.41 |

Thus, one may calculate selectivity, that is, the ratio of aromatics to aliphatics in the solvent phase at 4.73.

[toluene]solvent/[heptane]solvent=10.64/2.25=4.73

EXAMPLE 3a

Sulfolane/Dimethyl Sulfone Experiment

The procedure of Example 3 was repeated with the modification that the 120.0 grams of sulfolane was replaced with a mixture of 90.0 g of sulfolane and 30.0 g of dimethyl sulfone.

The selectivity, that is, the ratio of aromatics to aliphatics in the solvent phase was 5.5. The loading of toluene in the extractive solvent was 6.45 g.

EXAMPLE 4

Glycol Control Experiment

Charged in the equilibrium cell at room temperature was 120.0 g tetraethylene glycol (TEG). A mixture, 30.0 g of 1 part toluene to 1 part n-heptane was added, and the heating was increased to bring the mixture to reflux. Reflux continued for 15 minutes in the closed system; at this point the vapor temperature was 100–101° C. Samples of both the solvent and feed phases were withdrawn by syringe through the lower sample port for GC analysis.

The solvent and feed phase samples were diluted with acetone prior to GC analysis; the vapor condensate sample was analyzed neat. Values for solvent, feed, and vapor phase compositions were reported as an average of two experiments.

The following results were obtained:

TABLE 4

Liquid-liquid Equilibrium (LLE) data for glycol experiment.

|  | wt % toluene | wt % heptane |
|---|---|---|
| Solvent phase | 6.24 | 1.82 |
| Feed phase | 22.9 | 45.8 |

Thus, one may calculate selectivity, that is, the ratio of aromatics to aliphatics in the solvent phase at 3.43.

[toluene]solvent/[heptane]solvent=6.24/1.82=3.43

EXAMPLE 4a

Glycol-Dimethyl Sulfone Experiment

The procedure of Example 3 was repeated with the modification that the 120.0 grams of tetraethylene glycol was replaced with a mixture of 90.0 grams of tetraethylene glycol and 30.0 grams of dimethyl sulfone.

The selectivity, that is, the ratio of aromatics to aliphatics in the solvent phase was 5.1. The loading of toluene in the extractive solvent was 5.04 g.

EXAMPLE 5

Experimental Protocol for Loading Experiments

'Loading' relates to the weight of aromatic compound(s) extracted into the extractive solvent phase produced by an extractive distillation.

The apparatus and procedure used in the selectivity experiments above (Examples 1–4) were adapted for hydrocarbon loading experiments as follows. A hydrocarbon mixture containing 0.5 parts by weight, 5.6 g of toluene and 0.5 parts by weight, 5.6 g of n-heptane were added to the above-described extractive distillation apparatus, along with four parts by weight, 44.8 g of an extractive distillation composition of a specified composition (selected from dimethyl sulfoxide, sulfolane, and tetraethylene glycol, a 50:50 mixture of dimethyl sulfoxide and dimethyl sulfone, a 25:75 mixture of dimethyl sulfone and sulfolane, and a 25:75 mixture of dimethyl sulfone and tetraethylene glycol, respectively). The weight of the resulting mixture was held constant at 56.0±2 g between experiments.

The mixture was then heated to its boiling point, and a measured volume (2.0 ml) of the extractive distillate phase distilled overhead (hydrocarbon raffinate) was collected and analyzed using gas chromatography, for heptane and toluene. The weight and volume of the liquid mixture remaining in the lower portion of the extractive distillation apparatus was measured by pouring the hot mixture into a heated, tared measuring cylinder, and weighing on an analytical balance. In most experiments, the mixture was a two-phase mixture, comprising an extractive solvent phase (bottom phase) and a hydrocarbon feed phase (top phase). After removing the hydrocarbon feed phase by pipette, the weight of the remaining extractive phase was determined. The weight of the hydrocarbon feed phase removed by pipette was calculated by difference. Aliquots of both top and bottom phases were diluted in a weighed amount of methylene chloride and analyzed using gas chromatography for heptane and toluene. A mass balance for the system was calculated, and found in good agreement with the total initial charge (see Table 5, column 4, row 1–4).

Changes in aromatics loading or capacity were determined by GC analysis, and reported as the change in weight % toluene in the extractive solvent phase, relative to a reference experiment containing unmodified solvent. Thus, percent loading may be defined as follows:

% Loading=$((wt\ toluene_{expt1}-wt\ toluene_{ref})/wt\ toluene_{ref})\times 100$ The following results were obtained:

TABLE 5

Loading data according to Experiment 5.

| Extractive Solvent | wt toluene, g |
|---|---|
| 50:50 DMSO/DMSO$_2$ | 8.5 |
| DMSO | 10.1 |
| sulfolane | 6.08 |
| TEG | 4.48 |

Table 6 summarizes the selectivity and loading data from Examples 1. Through 5.

TABLE 6

Selectivity/loading data according to Examples 1–5.

| Extractive Dist. Composition | Aromatics Loading (gr.) | Toluene/Heptane Selectivity |
|---|---|---|
| TEG | 4.48 | 3.4 |
| Sulfolane | 6.68 | 4.7 |
| DMSO | 10.1 | 2.1 |
| 50:50 DMSO/DMSO2 | 8.5 | 5.3 |
| 25:75 DMSO2/sulfolane | 6.45 | 5.5 |
| 25:75 DMSO2/TEG | 5.04 | 5.1 |

Extractive solvent properties may be represented graphically by plotting the selectivity and loading data, as shown in FIG. 1.

Commercial aromatic extraction processes employ primarily three extractive solvents, sulfolane, glycols and DMSO. Sulfolane based aromatic extraction units operate at higher energy efficiency, that is, produce relatively greater volume of aromatic extracts than glycol based 'Udex' processes. The well recognized advantage of the sulfolane process relative to 'Udex', glycol based, technologies is consistent with the data from FIG. 1. Sulfolane exhibits higher selectivity and loading as an aromatic extraction solvent relative to tetraethylene glycol (TEG), the solvent in modern glycol units. Although DMSO exhibits high aromatic loading, it does so at the expense of selectivity. Relatively high amounts of non-aromatic hydrocarbons are entrained in this solvent. Further purification is accomplished by re-circulation in the unit, with attendant energy expenditures.

Superior aromatic extraction solvents and compositions possess both high loading capacity for aromatics and high selectivity for aromatic over non-aromatic hydrocarbons. In other words, the superior aromatic extraction solvents and compositions would occupy a position in loading-selectivity space located in the upper right hand corner of FIG. 1. It has been discovered that compositions comprising combinations of organic sulfones and organic sulfoxides can provide such superior combinations of both selectivity and loading. For example, as can be seen in FIG. 1, DMSO/DMSO$_2$ mixtures can give a better combination of selectivity and loading than any one of the three commercial solvent systems, and thus embody a significant improvement in the state of the art. Indeed, the extractive distillation compositions of the present invention afford an unexpected and desirable marriage of extraction performance, i.e. selectivity/loading advantages.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A distillation process comprising at least partially separating mixtures of aromatic and non-aromatic hydrocarbon compounds employing an extractive distillation composition comprising:
   a. at least one organic sulfoxide of the formula $R_1$—SO—$R_2$, and b. at least one acyclic organic sulfone of the formula $R_3$—SO$_2$—$R_4$ wherein $R_1$, $R_2$, $R_3$, and $R_4$ have at least one carbon atom and can be the same or different, and
   wherein the at least one organic sulfoxide is present in an amount effective to provide improved separation of the aromatic and non-aromatic hydrocarbon compounds, as compared to a process employing the same extractive distillation composition not comprising the organic sulfoxide.

2. The process of claim 1 wherein the improved separation of the aromatic and non-aromatic hydrocarbon compounds comprises an increase in the selectivity of the separation of the aromatic and non-aromatic hydrocarbon compounds.

3. The process of claim 1 wherein the improved separation of the aromatic and non-aromatic hydrocarbon compounds comprises an increase in the loading of the aromatic hydrocarbon compounds in the extractive distillation composition after extractive distillation.

4. The process of claim 1 wherein the improved separation of the aromatic and non-aromatic hydrocarbon compounds comprises an increase in the selectivity of the separation of the aromatic and non-aromatic hydrocarbon compounds, and a simultaneous increase in the loading of the aromatic hydrocarbon compounds in the extractive distillation composition after extractive distillation.

5. The process of claim 1 additionally comprising water.

6. The process of claim 1 comprising from about 0.1 parts to about 15 percent water.

7. The process of claim 1 wherein the at least one organic sulfoxide is a dialkyl, diaryl, mixed aryl alkyl or cyclic sulfoxide.

8. The process of claim 1 wherein the at least one acyclic organic sulfone is a dialkyl, diaryl, or mixed aryl alkyl sulfone.

9. The process of claim 1 wherein $R_1$, $R_2$, $R_3$, and $R_4$ independently have from one to four carbon atoms.

10. The process of claim 1 wherein the at least one organic sulfoxide is dimethyl sulfoxide.

11. The process of claim 1 wherein the at least one organic sulfone is dimethyl sulfone.

12. The process of claim 1 wherein the at least one organic sulfone is dimethyl sulfone and the at least one organic sulfoxide is dimethyl sulfoxide.

13. The process of claim 12 additionally comprising water.

14. The process of claim 1 wherein the at least one organic sulfoxide is present at a concentration of greater than about 20 percent by weight or volume.

15. The process of claim 1 wherein the at least one organic sulfoxide is present at a concentration of from about 22 to about 78 weight percent.

16. The process of claim 1 wherein the at least one organic sulfone is present at a concentration of greater than about 21 percent by weight or volume.

17. The process of claim 1 wherein the at least one organic sulfone is present at a concentration from about 22 to about 78 weight percent.

18. The process of claim 1 wherein the at least one organic sulfone is present at a concentration of greater than about 21 weight percent, and the at least one organic sulfoxide is present at a concentration of greater than about 21 weight percent.

19. The process of claim 1 wherein the hydrocarbon compounds comprises a mixture of aromatic and aliphatic compounds.

20. The process of claim 1 wherein the hydrocarbon compounds are a BTX stream.

21. The process of claim 1 wherein the hydrocarbon compounds comprise benzene, toluene, p-xylene, m-xylene, o-xylene, ethylbenzene, or a mixture thereof.

22. A process for separating hydrocarbon compounds of similar volatility by extractive distillation, comprising the steps of:
   a. contacting a feed mixture with an extractive distillation composition, wherein the feed mixture comprises at least
      i. at least one first hydrocarbon compound, and
      ii. at least one second hydrocarbon compound; and
   b. distilling the feed mixture within an extractive distillation zone to at least partially separate the feed mixture into a first stream enriched in the first hydrocarbon compound, and a second stream enriched in the second hydrocarbon compound;

wherein the extractive distillation composition comprises
   i. dimethyl sulfone, and
   ii. greater than about 21 percent by volume of dimethyl sulfoxide.

23. The process of claim 22 further comprising water.

24. The process of claim 22 further comprising from about 0.1 to about 15 parts by weight of water.

25. The process of claim 22 comprising greater than about 20 percent by volume of dimethyl sulfone.

26. The process of claim 22, wherein the first hydrocarbon compound comprises at least one saturated hydrocarbon residue, and the second hydrocarbon compound comprises at least one carbon-carbon double bond.

27. The process of claim 22, wherein the first hydrocarbon compound is a $C_7$–$C_{10}$ aliphatic compound.

28. The process of claim 22, wherein the second hydrocarbon compound is a $C_6$–$C_{10}$ substituted benzene compound.

29. The process of claim 22 wherein the second hydrocarbon compound is benzene, toluene, p-xylene, m-xylene, o-xylene, ethylbenzene, or a mixture thereof.

30. The process of claim 22 wherein the first and/or second hydrocarbon compounds form an azeotropic mixture.

31. The process of claim 22 wherein the first and second hydrocarbon compounds have normal boiling points that differ by less than about 5° C.

32. The process of claim 22 wherein the feed mixture comprises a BTX stream.

33. The process of claim 22 further comprising treating the second stream to separate the second hydrocarbon compound from the extractive distillation composition.

34. A distillation process comprising at least partially separating mixtures of aromatic and non-aromatic hydrocarbon compounds employing an extractive distillation composition comprising:
   a. greater than about 21% by volume of dimethylsulfoxide, and
   b. greater than about 21% by volume of dimethylsulfone.

35. The process of claim 34 further comprising water.

36. The process of claim 34 wherein the hydrocarbon compounds comprise benzene, toluene, p-xylene, m-xylene, o-xylene, ethylbenzene, or a mixture thereof.

37. A process for separating hydrocarbon compounds of similar boiling points by extractive distillation, comprising the steps of:
   a. introducing a feed mixture into an extractive distillation zone having an upper portion and a lower portion, wherein the feed mixture comprises at least
      i. a first hydrocarbon compound comprising a $C_7$–$C_{10}$ aliphatic compound, and
      ii. a second hydrocarbon compound comprising benzene, toluene, ortho-xylene, meta-xylene, para-xylene, or a mixture thereof; and
   b. introducing an extractive distillation composition into the upper portion of the extractive distillation zone; and
   c. distilling the feed mixture to at least partially separate the feed mixture into a first stream rich in the first hydrocarbon compound, and a second stream rich in the second hydrocarbon compound;
   wherein the extractive distillation composition comprises:
      i. from about 25 to about 75 parts by weight of dimethylsulfoxide,
      ii. from about 25 to about 75 parts by weight of dimethylsulfone.

38. The process of claim 1 wherein the at least one organic sulfone is a dialkyl sulfone having from three to nine total carbon atoms.

* * * * *